United States Patent [19]

Kawakami et al.

[11] Patent Number: 4,997,914

[45] Date of Patent: Mar. 5, 1991

[54] METHOD FOR SEPARATING AND PURIFYING LACTOFERRIN FROM MILK BY USE OF SULFURIC ESTER

[75] Inventors: Hiroshi Kawakami, Kawagoe; Morimasa Tanimoto, Sayama; Shunichi Dousako, Urawa, all of Japan

[73] Assignee: Snow Brand Milk Products Co., Ltd., Sappore, Japan

[21] Appl. No.: 273,337

[22] PCT Filed: Apr. 7, 1988

[86] PCT No.: PCT/JP88/00353

§ 371 Date: Nov. 9, 1988

§ 102(e) Date: Nov. 9, 1988

[87] PCT Pub. No.: WO88/08006

PCT Pub. Date: Oct. 20, 1988

[30] Foreign Application Priority Data

Apr. 10, 1987 [JP] Japan ................................. 62-88450

[51] Int. Cl.$^5$ .......................... A23J 1/20; C07K 3/18; C07K 3/20
[52] U.S. Cl. .................................. 530/395; 530/366; 530/397; 530/400; 530/832
[58] Field of Search ............... 530/366, 395, 400, 397, 530/832

[56] References Cited

U.S. PATENT DOCUMENTS

| | | | |
|---|---|---|---|
| 4,096,136 | 6/1978 | Ayers et al. | 530/359 |
| 4,175,183 | 11/1979 | Ayers | 536/57 |
| 4,178,439 | 12/1979 | Ayers et al. | 536/57 X |
| 4,436,658 | 3/1984 | Peyrouset et al. | 530/366 |
| 4,667,018 | 5/1987 | Prieels et al. | 530/832 X |
| 4,668,771 | 5/1987 | Kawakami et al. | 530/366 |
| 4,791,193 | 12/1988 | Okonogi et al. | 530/366 X |

FOREIGN PATENT DOCUMENTS 2179947 3/1987 United Kingdom .

OTHER PUBLICATIONS

Fieser et al., "Reagents for Organic Synthesis", John Wiley & Sons, New York, (1967), pp. 1000-1001.
Febs Letters, vol. 144, (1982), pp. 1-5, Boesman-Finkelstein et al.
Pediatric Research, vol. 20, (1986), pp. 197-201, Davidson et al.
Comp. Biochem. Physiol., vol. 78B, (1984), pp. 575-580, Wang et al.
Merck Index, 9th ed., p. 383, 1976.
Biotechnology, A Textbook of Industrial Microbiology, (1984), Crueger et al., 100-101.
Proteins and Enzymes, Prentice-Hall, Bell et al., (1988), pp. 22-31.
Kirk-Othmer, Encyclopedia of Chemical Technology, vol. 4, 3rd Edition, (1978), pp. 14-15, vol. 6, 3rd Ed., p. 42, vol. 12, p. 46, 48-53.
Biochemistry, Stryer, 3rd Edition, p. 346, (1988).
The Condensed Chemical Dictionary, 10th Ed., Howley, (1981), p. 522.
Merck Index, 10th Ed., (1983), pp. 681 and 120.
Febs Letters, vol. 109, (1980), 180-184, (Blackburg et al.).
The Biochemical Journal, vol. 124, (1971), 677-683, Iverius Sigma Catalog, (1990), pp. 1566-1567.
Analytical Biochemistry, 162, 296-300, (1987), Foley et al.

Primary Examiner—Howard E. Schain
Attorney, Agent, or Firm—Oblon, Spivak, McClelland, Maier & Neustadt

[57] ABSTRACT

A method for separating and purifying lactoferrin from milk is disclosed, which method comprises the steps of bringing raw milk containing lactoferrin into contact with a sulfuric ester of a crosslinked polysaccharide so that lactoferrin may be adsorbed by the sulfuric ester, and then eluting the adsorbed lactoferrin. The elution of the adsorbed lactoferrin is preferably conducted by the use of a buffer solution containing a 0.4–1.5 M aqueous sodium chloride solution.

5 Claims, No Drawings

METHOD FOR SEPARATING AND PURIFYING LACTOFERRIN FROM MILK BY USE OF SULFURIC ESTER

BACKGROUND OF THE INVENTION

(1) Field of the Invention

The present invention relates to a method for separating and purifying lactoferrin, which is a pharmacologically important milk protein having various physiological activities, from milk containing lactoferrin.

(2) Description of the Prior Art

Lactoferrin is an iron-binding glycoprotein present in an exocrine liquid such as milk and has a variety of physiological activities such as bateriostasis against pathogenic bacteria, adjusting function of leukocyte differentiation, build-up function of germicidal power, multiplicative function of lymphocyte and adjusting function of iron absorption. For that reason, it can be said that lactoferrin is a milk protein which is important not only from a nutritional viewpoint but also a pharmacological viewpoint.

As a result, many attempts have heretofore been made to develop methods for separating and purifying lactoferrin from milk. However, since lactoferrin is a protein having a very reactive molecular structure and interacting with other milk proteins, it has been difficult to separate and purify lactoferrin in a high purity and in a high yield by a simple and easy operation.

In other words, in order to separate high-purity lactoferrin, an intricate process and a long period of time is necessary. In addition, the recovery efficiency of lactoferrin is disadvantageously low.

Recently, a separating and purifying method for lactoferrin has been reported in which a raw liquid is passed through an affinity column where heparin having physiological affinity to lactoferrin is fixed on a carrier for chromatography such as Cephalose CL-6B (made by Pharmacia Labs., Inc.) with the aid of CNBr or the like, whereby lactoferrin is separated and purified therefrom (Blackberg, L. et al, FEBS LETT., 109, p. 180, 1980).

However, heparin is extracted and purified from the livers or intestines of pigs, cattle or the like, and differences in the source of extraction lead to differences in heparin properties. For this reason, it is hard to obtain a great deal of heparin having uniform properties. Further, heparin is expensive. As a result, the method of separating and purifying lactoferrin from milk by the use of the affinity carrier for chromatography having heparin bound and fixed thereto can be practiced only on an experimental scale. In other words, the above suggested known method is impracticable on an industrial scale. Further, the above method has the problem that heparin fixed on the carrier might be peeled therefrom and inconveniently mixed with separated lactoferrin on occasion.

SUMMARY OF THE INVENTION

A first object of the present invention is to provide a method for separating and purifying lactoferrin from milk on an industrial scale by a simple and easy operation. A second object of the present invention is to provide a method for separating and purifying lactoferrin from milk extremely effectively in a high yield and a high purity.

The present invention is characterized by bringing raw milk containing lactoferrin into contact with a sulfuric ester of a crosslinked polysaccharide so that lactoferrin may be adsorbed by the sulfuric ester, then eluting and recovering the thus adsorbed lactoferrin therefrom.

DESCRIPTION OF THE PREFERRED EMBODIMENT

A sulfuric ester of a crosslinked polysaccharide used in the present invention has physiological affinity to lactoferrin in common with heparin and is superior in physical stability to heparin. This sulfuric ester can be prepared in quantity by esterifying, with anhydrous sulfuric acid or chlorosulfonic acid, a polysaccharide such as agarose, cellulose or chitin which has been crosslinked with a crosslinking agent (e.g., epichlorohydrin). The above crosslinked polysaccharide is commercially available.

However, since agarose is soft, it is liable to deforming. Thus in considering manufacturing lactoferrin on an industrial scale, a carrier such as cellulose or chitin is preferably used.

Since the sulfuric ester of such crosslinked polysaccharides is insoluble in an aqueous solvent and is excellent in physical stability, an affinity column charged with this sulfuric ester can sufficiently withstand the passage of a raw liquid on an industrial scale.

Examples of the sulfuric esters of the cross-linked polysaccharides include sulfated Cellulofine prepared by esterifying crosslinked cellulose (having an amino group) with sulfuric acid, and sulfated Chitopearl prepared by esterifying crosslinked chitosan (which is crosslinked via an amino group) with sulfuric acid.

The separation and purification of lactoferrin from milk by the use of the sulfuric ester of a crosslinked polysaccharide may be suitably carried out by passing raw milk through a column charged with a sulfuric ester carrier, or by mixing raw milk with the sulfuric ester and then stirring the resulting mixture.

In the present invention, the contact of the sulfuric ester with raw milk containing lactoferrin is conducted at a temperature of 50° C. or less, preferably at room temperature. First, raw milk is passed through the column, and the fraction which has not been adsorbed by the column is then eluted. Afterward, the column is washed with a 0.3M aqueous sodium chloride solution or a 0.01–0.02M buffer solution of, for example, sodium phosphate, tris-HCl, ammonia-HCl or Veronal (trade name), which contains a 0.3M aqueous sodium chloride solution and which has a pH of 5.0 to 9.0. Next, a 0.4M–1.5M aqueous sodium chloride solution, preferably a 1.0M aqueous sodium chloride solution or the above-mentioned buffer solution containing a 1.0M aqueous sodium chloride solution, is passed through the column, so that lactoferrin adsorbed on the column is eluted, whereby lactoferrin can be separated from the milk.

Alternatively, in the present invention, lactoferrin can be separated as follows: First, raw milk is mixed with the sulfuric ester, and this ester is then recovered by means of decantation or centrifugation. The thus recovered sulfuric ester on which lactoferrin is adsorbed is washed with a 0.3M aqueous sodium chloride solution or a buffer solution containing a 0.3M aqueous sodium chloride solution and having a pH of 5.0 to 9.0, and the ester is then again recovered by means of decantation or centrifugation. A 0.4–1.5M aqueous sodium chloride solution or the above buffer solution containing a 0.4–1.5M aqueous sodium chloride solution is added to the thus recovered ester, and washing is carried out. Afterward, the mixture is allowed to stand. By means of decantation or centrifugation, a supernatant liquid containing lactoferrin is collected, whereby lactoferrin is separated from the milk.

The thus separated lactoferrin is desalted by the use of an electrodialysis (ED) apparatus or a reverse osmosis (RO) apparatus, then freeze-dried, and afterward preserved at 40° C. or less, preferably at 4° C. In this regard, reproduction of the ester from which lactoferrin has been separated can be achieved by washing the ester with a 2M aqueous sodium chloride solution and then passing a 0.15M aqueous sodium chloride solution through it.

The thus-obtained lactoferrin has a purity of 95% or more, as confirmed by a chart of SDS electrophoresis.

Examples of the raw milks used in the present invention include colostrum, transitional milk, ordinary milk and final milk of mammals such as humans, cattle and sheep as well as low temperature-sterilized milk and whey.

When lactoferrin is separated and refined from these raw milks in accordance with the present invention, there are no problems such as the necessity of a long treatment time and a low recovery of lactoferrin which can be attributed to the complicated operation and processes of conventional methods.

In other words, according to the present invention, lactoferrin can be recovered in a high purity and in a high yield. In particular, the present invention is intended to adsorb lactoferrin present in milk by a crosslinked polysaccharide sulfuric ester alone, which is excellent in physical stability, and therefore there are no problems as in the conventional method in which an affinity carrier for chromatography containing the fixed heparin is used, one of the above problems being that heparin is peeled from the carrier. In the present invention, since adsorbed lactoferrin can be easily eluted by using an aqueous sodium chloride solution alone, the separation of lactoferrin can be performed very efficiently.

In addition, since the crosslinked polysaccharide sulfuric ester used in the present invention can be prepared by esterifying, with sulfuric acid, a crosslinked polysaccharide, a raw material of which is cellulose or chitin abundant in nature, this ester can be manufactured in quantity and is conveniently available at a low cost.

From results measured in accordance with the process suggested by Woodworth et al. (Protides Biol. Fluids Proc. Colloq., 14, p. 37, 1969), it has been shown that the lactoferrin separated by the present invention has an iron-binding capacity of 1.3 to 2.1 milligrams of Fe per gram of lactoferrin, which proves that the lactoferrin possesses its original iron-binding capacity intact. Therefore, the lactoferrin obtained by the present invention can be utilized as a preventive medicine to protect infants from pathogenic bacteria which require iron and as a therapeutic medicine against various symptoms based on the pathogenic bacteria.

Moreover, in the present invention, the lactoferrin solution separated and purified by the process described above may be mixed with ferric chloride directly and then stirred, and the mixture may be then passed through a ED apparatus or an RO apparatus in order to separate iron-saturated lactoferrin therefrom with ease. Accordingly, the present invention is particularly useful to facilitate the absorption of iron in the intestine. In this regard, it has been already reported that iron-saturated lactoferrin has the effect of improving the absorption of iron in the intestine (Cox, T. M. et al., Biochim. Biophys. Acta, 588, p. 120, 1979).

The present invention will now be described in detail by way of examples.

EXAMPLE 1

Commercially available Cellulofine (trade name), which is a crosslinked cellulose, was esterified with anhydrous sulfuric acid in a conventional manner to form sulfated Cellulofine, and a column having a diameter of 2 cm and a length of 20 cm was charged with 50 ml of the thus sulfated Cellulofine. Through this column, 50 ml of defatted human colostrum was then passed at a rate of 10 ml/minute. Afterward, the column was washed with 300 ml of a 0.3M aqueous sodium chloride solution, and lactoferrin adsorbed on the column was then eluted with 100 ml of a 1.0M aqueous sodium chloride solution. The thus-obtained lactoferrin solution was subjected to dialysis in exchange for a sufficient amount of deionized water, followed by freeze-drying, thereby obtaining 110 mg of human lactoferrin. The purity of the recovered human lactoferrin was measured at 97% by a chart of SDS polyacrylamide gel electrophoresis, and the amount of combined iron was measured at 0.2 mg of Fe per gram of protein by means of a serum iron measuring kit (made by Wako Junyaku Co., Ltd.). Further, it was confirmed by the Woodworth process that the total iron bonding capacity was 100%.

EXAMPLE 2

Commercially available Chitopearl (trade name), which is a crosslinked chitosan was esterified with anhydrous sulfuric acid in a conventional manner to form sulfuric acid-esterified chitopearl, and a column having a diameter of 8 cm and a length of 20 cm was charged with 1 liter of the thus sulfated Chitopearl. Through this column, 50 liters of defatted bovine milk was then passed at a rate of 20 liters/hour. Afterward, the column was washed with 5 liters of a 0.3M aqueous sodium chloride solution, and lactoferrin adsorbed on the column was then eluted with 3 liters of a 1.0M aqueous sodium chloride solution. The thus-obtained lactoferrin solution was desalted by a small-sized type ED apparatus (TS-210; made by Tokuyama Soda Co., Ltd.), and was concentrated tenfold by a UF apparatus (DH-2; made by Amicon Co., Ltd.), followed by freeze-drying.

The amount of the thus recovered lactoferrin was 6 g. The purity of the lactoferrin was measured at 95%, and the amount of combined iron was 0.2 mg of Fe per gram of protein. Further, it was confirmed that the total iron bonding capacity was 98%.

EXAMPLE 3

In this example, lactoferrin was separated and purified by a batch system by mixing raw milk with a sulfuric ester.

Through the sulfated Chitopearl used in Example 2, first a 2.0M aqueous sodium chloride solution and then a 0.15M aqueous sodium chloride solution were passed to reproduce the sulfated Chitopearl.

One liter of the thus reproduced sulfated Chitopearl was mixed with 100 liters of cheese whey and then stirred for 1 hour, and the resulting mixture was washed with 5 liters of a 0.3M aqueous sodium chloride solution. Afterward, lactoferrin adsorbed on the sulfated Chitopearl mixture was eluted with 3 liters of a 1.0M aqueous sodium chloride solution. To the thus obtained lactoferrin solution, 50 mg of ferric chloride was added, followed by further stirring. After a reverse osmosis apparatus (MRG 10 moled; made by Mitsubishi Rayon Co., Ltd.) was used to perform desalting and concentration (tenfold), freeze-drying was carried out to obtain 4.8 g of iron-saturated bovine lactoferrin. The purity of the recovered bovine lactoferrin was 95%, and the amount of combined iron was 1.3 mg of Fe per gram of protein. Further, it was confirmed that the saturation degree of iron was 93% or more.

What is claimed is:

1. A method for separating and purifying lactoferrin from raw milk, comprising the steps of:
    (a) contacting said raw milk with a resin comprising a sulfuric ester of a cross-linked polysaccharide in order to adsorb lactoferrin onto said resin, and
    (b) eluting said adsorbed lactoferrin.

2. A method according to claim 1 wherein said contact is achieved by passing said raw milk containing lactoferrin through an affinity column comprising said sulfuric ester of said crosslinked polysaccharide.

3. A method according to claim 1 wherein said adsorbed lactoferrin is eluted with a buffer solution containing a 0.4–1.5M aqueous sodium chloride solution and is then subjected to electrodialysis or reverse osmosis to desalt the lactoferrin solution.

4. A method according to claim 2 wherein said adsorbed lactoferrin is eluted with a buffer solution containing a 0.4–1.5M aqueous sodium chloride solution and is then subjected to electrodialysis or reverse osmosis to desalt the lactoferrin solution.

5. A method according to claim 1 wherein said crosslinked polysaccharide is cellulose or chitin.

* * * * *